United States Patent [19]

Cipriani et al.

[11] 3,966,782

[45] June 29, 1976

[54] COPPER BASE METALORGANIC COMPOUNDS AND PROCESS FOR THE PREPARATION THEREOF

[75] Inventors: Gioacchino Cipriani; Emilio Perrotti, both of San Donato Milanese, Italy

[73] Assignee: Snam Progetti S.p.A., San Donato Milanese, Italy

[22] Filed: Nov. 15, 1974

[21] Appl. No.: 524,311

[30] Foreign Application Priority Data
Nov. 21, 1973 Italy.................................... 31501/73

[52] U.S. Cl. ........................ 260/438.1; 252/431 N; 260/464; 260/551 R
[51] Int. Cl.² ............................................ C07F 1/08
[58] Field of Search ................................ 260/438.1

[56] References Cited
UNITED STATES PATENTS
3,221,026  11/1965  Webster........................ 260/438.1 X
3,644,453  2/1972  Onsager........................... 260/438.1

FOREIGN PATENTS OR APPLICATIONS
571,384  2/1959  Canada

OTHER PUBLICATIONS
Chemical Abstracts, vol. 63, 12649g (1965).

*Primary Examiner*—Helen M. S. Sneed
*Attorney, Agent, or Firm*—Ralph M. Watson

[57] ABSTRACT

A copper compound having the general formula:

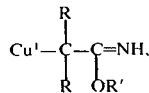

wherein the copper is in the $^{+}1$ oxidation state; R, the same or different, is hydrogen, methyl or phenyl; and R' is ethyl or methyl, is prepared by reacting a monovalent copper salt such as CuBr with an alkali metal alkoxide in the presence of a mixture of an alcohol and a nitrile under anhydrous conditions and in an atmosphere of an inert gas.

3 Claims, No Drawings

COPPER BASE METALORGANIC COMPOUNDS AND PROCESS FOR THE PREPARATION THEREOF

The present invention relates to the preparation of novel copper metalorganic compounds and to the compounds obtained thereby.

The inventive copper compounds can be employed for carrying out hydrolysis reactions of nitriles to amides and transformation reactions of olefins to nitriles and dinitriles and can be described by the following general formula

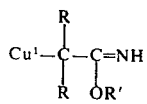

in which copper is in the oxidation state $^{+}1$, R, the same or different, is hydrogen, an alkyl or aryl radical, R' is an alkyl or an aryl radical.

The process for the preparation of the inventive compounds substantially consists in reacting monovalent copper salts with alkali metal alkoxides in the presence of a mixture formed by alcohol and the nitrile we are interested in, which respectively have the general formula R'OH and RR'CHCN wherein R' and R have the aforesaid meanings, the reaction being carried out under an inert gas atmosphere and in the presence of an inert solvent selected from aliphatic, aromatic, cycloaliphatic, hydrocarbons and tetrahydrofuran.

The reaction can be described by the following scheme

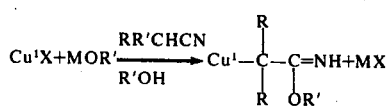

wherein M is an alkali metal, preferably lithium, sodium or potassium and X is a monovalent anion selected from halides, $ClO_4^-$ $BF_4^-$ etc.

Alternatively the inventive process can be carried out in two stages, in the first of which the monovalent copper compound reacts with the alkali metal alkoxide in an inert solvent according to the scheme

to give an intermediate product which can be isolated as such or further reacted with nitrile to obtain the inventive compounds.

This is an interesting feature of the present invention, since the obtained intermediate product itself is a stable compound which, when isolated, can be stored for later use.

The reaction can be carried out in a wide temperature range provided that the reaction liquid phase is preserved. Particularly the reaction is carried out at temperatures ranging from 0° to 50°C.

Further working data will be more evident by examining the following examples, which better illustrate the invention without limiting the purposes thereof.

EXAMPLE 1

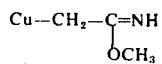

2.98 g. of CuBr were dissolved in 150 cc of anhydrous $CH_3CN$ previously degassed by Ar. A methyl alcohol solution of $LiOCH_3$, anhydrous and degassed by Ar, was prepared by dissolving 0.165 g. of metal Lithium in 100 cc of $CH_3OH$.

This solution was added, drop by drop and under an Ar atmosphere, to the cuprous solution, under stirring at room temperature. The precipitation of the product was immediate. The addition of $LiOCH_3$ was carried out over 30 minutes and, then, the whole was kept under stirring for about 2 hours. The white product was filtered and dried under vacuum. The yield was 1.42 g. (50% with respect to CuBr). When a double amount of $LiOCH_3$ was added to the cuprous solution, the other conditions being the same, 2.20 g. of product were obtained (79.5% with respect to CuBr).

The analytical determination of C H N Cu carried out on the product, the results of the thermal pyrolisis directly performed at the mass spectrometer (methyl alcohol and $CH_3CN$ development), the I.R. spectrum ($\nu_{NH}$ very weak at 3300 cm$^{-1}$, $\nu_{C=N}$ very strong and broad at 1650 cm$^{-1}$, $\nu_{C-O}$ broad and strong at 1185 cm$^{-1}$, and sharp and averagely strong at 1070 cm$^{-1}$, no band awardable to $\nu_{Cu-O}$ which generally are at 520 cm$^{-1}$) agreed upon a minimum formula $CuOCH_3 \cdot CH_3CN$ and a structure

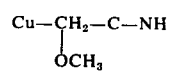

EXAMPLE 2

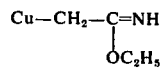

The procedure was substantially the same as the one followed for the homologous methyl compound. 3.01 g. of CuBr were dissolved in 150 cc of $CH_3CN$. To this solution was added a solution of $LiOC_2H_5$ obtained from 0.360 g. of Li in 100 cc of ethyl alcohol. The addition of $LiOC_2H_5$ was performed over 30 minutes and then the whole was kept under stirring for about 2 hours.

The product was filtered and dried under vacuum. 2.30 g. of product were obtained (73.5 % with respect to CuBr).

The analytical determination of C H N Cu carried out on the product, the I.R. spectrum ($\nu_{N-H}$ very weak at 3300 cm$^{-1}$, $\nu_{C=N}$ very strong at 1650 cm$^{-1}$, $\nu_{O-C}$ at 1195 and 1060 cm$^{-1}$, no band awardable to $\nu_{Cu-O}$) agreed upon a minimum formula $CuOC_2H_5 \cdot CH_3CN$ and a structure $Cu - CH_2 - C(OC_2H_5)= NH$.

EXAMPLE 3

3.05 g. of CuBr were suspended in 75 cc of anhydrous THF (tetrahydrofuran) ($H_2O$ < 10 ppm) and carefully degassed by Ar.

To this solution was added 30 cc of a methanol solution containing $LiOCH_3$ obtained by dissolving 0.342 g. of metal Li in methyl alcohol. The addition of $LiOCH_3$ was performed over 30 minutes and then the whole was kept under stirring for about 2 hours. The product was filtered and dried under vacuum. 1.60 g. were obtained (58% with respect to Cu).

The analytical determination of C H Li Cu carried on the product, I.R. specrrum ($\nu_{CH}$ at 2800 cm$^{-1}$, $\nu_{O-C}$ at 1060 cm$^{-1}$, $\nu_{Cu-O}$ at 530 cm$^{-1}$) agreed upon a minimum formula CuOCH$_3$. LiOCH$_3$ which probably had the structure Cu(OCH$_3$)$_2$ Li.

EXAMPLE 4

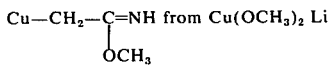

0.79 g. of Cu(OCH$_3$)$_2$Li were suspended in a solvent formed by 40 cc of CH$_3$OH and 60 cc of CH$_3$CN under carefully anhydrous conditions and very anhydrous environnement (Ar). The whole was kept under stirring at room temperature. After three hours the product was filtered and dried under vacuum. The transformation into

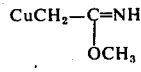

was selective and quantitative.

EXAMPLE 5

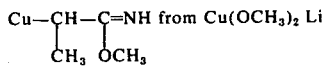

0.500 g. of Cu(OCH$_3$)$_2$ Li were suspended in 15 cc of anhydrous and carefully degassed OH$_3$CH at the temperature of 5°C. The whole was kept under stirring for about half an hour. Then 30 cc of anhydrous propionitrile were added and the whole was brought to room temperature. The whole was kept under stirring for about 3 hours. The product was filtered at a yield of 0.110 g. (19.5%). In time, another 90 mg precipitated from the mother liquor. Therefore the total yield was about 36%.

The analytical determination of C H N Cu carried out on the product, I.R. spectrum ($\nu_{N-H}$ at 3280 cm$^{-1}$, very weak, $\nu_{C=N}$ at 1650 cm$^{-1}$ very strong, $\nu_{C-O}$ at 1180 cm$^{-1}$ and at 1085 cm$^{-1}$, no band awardable to $\nu_{Cu-O}$) agreed upon a minimum formula CuOCH$_3$ . CH$_3$CH$_2$CN and a structure

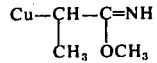

EXAMPLE 6

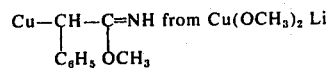

0.534 g. of Cu(OCH$_3$)$_2$ Li were suspended in 50 cc of anhydrous methyl alcohol carefully degassed by Ar, at a temperature of 50°C. Then 0.6 cc of phenylacetonitrile was added. The whole was brought to room temperature and kept under stirring for about 2 hours. The product was filtered: 90 mg. (10.6%). In time another mg 85 of product precipitated from the mother liquor. Total yield = 21%.

The analytical determination of C N H Cu carried out on the product, I.R. spectrum ($\nu_{C=N}$ at 1640 cm$^{-1}$, $\nu_{C-O}$ at 1215 and at 1125 cm$^{-1}$, no $\nu_{Cu-O}$ band) agreed upon a minimum formula Cu — OCH$_3$ . C$_6$H$_5$CH$_2$ — C = N and a structure

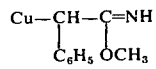

What we claim is:

1. A copper base metalorganic compound having the formula

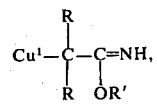

wherein the copper is in the $^{+1}$ oxidation state, R, the same or different, is a member of the group consisting of hydrogen, methyl, ethyl and phenyl and R', is methyl or ethyl.

2. The process of preparing the metalorganic compound of claim 1, which consists in reacting a monovalent copper salt having the formula Cu$^I$X, wherein X is a monovalent anion selected from the group consisting of halides, ClO$_4^-$ and BF$_4^-$, with an alkali metal alkoxide in the presence of a mixture of a nitrile represented by the formula RR'CHCN, wherein R is a member of the group consisting of hydrogen, methyl, ethyl and phenyl and R' is methyl or ethyl, and an alcohol represented by the formula R'OH, wherein R' is methyl or ethyl, under anhydrous conditions in the presence of an inert solvent selected from the group consisting of aliphatic, aromatic and cycloaliphatic hydrocarbons and tetrahydrofuran, in the liquid phase, and in an atmosphere of inert gas.

3. The process of preparing the metalorganic compound of claim 1, which consists in:
   a. preparing an intermediate having the formula Cu$^I$- (OR')$_2$ M, wherein R' is methyl or ethyl, and M is an alkali metal, by reacting an alkali metal alkoxide with a monovalent copper salt having the formula Cu$^I$X, wherein X is a monovalent anion selected from the group consisting of halides, ClO$_4^-$ and BF$_4^-$; and
   b. reacting said intermediate under anhydrous conditions with a nitrile having the formula RR'CHCN, wherein R is a member of the group consisting of hydrogen, methyl, ethyl and phenyl, and R' is methyl or ethyl;

each of said reactions being carried out in the liquid phase in an inert solvent selected from the group consisting of aliphatic, aromatic and cycloaliphatic hydrocarbons and tetrahydrofuran, in an atmosphere of inert gas.

* * * * *